US012778949B2

(12) United States Patent
Chen et al.

(10) Patent No.: US 12,778,949 B2
(45) Date of Patent: Nov. 3, 2026

(54) ARIPIPRAZOLE SUSTAINED-RELEASE MICROSPHERE AND PREPARATION METHOD THEREFOR

(71) Applicant: Zhuhai Livzon Microsphere Technology Co. Ltd., Zhuhai (CN)

(72) Inventors: Bin Chen, Zhuhai City (CN); Xia Yin, Zhuhai City (CN); Yanqing Wang, Zhuhai City (CN); Peng Xu, Zhuhai City (CN); Yuda Yang, Zhuhai City (CN); Miaoli Chen, Zhuhai City (CN); Weilun Ye, Zhuhai City (CN); Linyan LV, Zhuhai City (CN); Huijuan Xu, Zhuhai City (CN); Wenqi Lu, Zhuhai City (CN); Xiangsheng Kong, Zhuhai City (CN); Xiaoman Jiang, Zhuhai City (CN)

(73) Assignee: ZHUHAI LIVZON MICROSPHERE TECHNOLOGY CO. LTD., Zhuhai (CN)

( * ) Notice: Subject to any disclaimer, the term of this patent is extended or adjusted under 35 U.S.C. 154(b) by 292 days.

(21) Appl. No.: 18/584,867

(22) Filed: Feb. 22, 2024

(65) Prior Publication Data

US 2024/0269131 A1 Aug. 15, 2024

Related U.S. Application Data

(62) Division of application No. 17/055,540, filed as application No. PCT/CN2018/090345 on Jun. 8, 2018, now Pat. No. 11,951,104.

(30) Foreign Application Priority Data

May 16, 2018 (CN) ........................ 201810468934.6

(51) Int. Cl.
*A61K 31/496* (2006.01)
*A61K 9/00* (2006.01)
(Continued)

(52) U.S. Cl.
CPC .......... *A61K 31/496* (2013.01); *A61K 9/0019* (2013.01); *A61K 9/1694* (2013.01);
(Continued)

(58) Field of Classification Search
CPC .................................................... A61K 31/496
See application file for complete search history.

(56) References Cited

U.S. PATENT DOCUMENTS

2010/0203151 A1 8/2010 Hiraoka
2011/0217341 A1 9/2011 Sah

FOREIGN PATENT DOCUMENTS

CN 106727358 A1 * 3/2017
CN 106727358 A * 5/2017
(Continued)

*Primary Examiner* — Carlos A Azpuru
(74) *Attorney, Agent, or Firm* — Womble Bond Dickinson US LLP

(57) ABSTRACT

The present invention provides an aripiprazole sustained-release microsphere and a preparation method therefor. The microsphere comprises aripiprazole and polylactide-glycolide. The microsphere is of a spherical reticular skeleton structure, with reticular micropores distributed in the spherical surface, and aripiprazole filled in the micropores. The average particle diameter of the microsphere is less than 20 μm, and is suitable for a 5 gauge needle. The content of aripiprazole is 65%-80% of the total weight of the microsphere.

20 Claims, 6 Drawing Sheets

(51) Int. Cl.

| | |
|---|---|
| ***A61K 9/16*** | (2006.01) |
| ***A61K 47/26*** | (2006.01) |
| ***A61K 47/34*** | (2017.01) |
| ***A61K 47/38*** | (2006.01) |

(52) U.S. Cl.
CPC .............. *A61K 47/26* (2013.01); *A61K 47/34* (2013.01); *A61K 47/38* (2013.01)

(56) References Cited

FOREIGN PATENT DOCUMENTS

| | | | | |
|---|---|---|---|---|
| CN | 108498456 | B | * | 9/2018 |
| CN | 2018137627 | A1 | * | 9/2018 |
| WO | WO 2017/059106 | A1 | | 4/2017 |
| WO | WO 2018/137627 | A1 | | 8/2018 |

* cited by examiner

ARIPIPRAZOLE SUSTAINED-RELEASE MICROSPHERE AND PREPARATION METHOD THEREFOR

CROSS-REFERENCE TO RELATED APPLICATION(S)

The present invention is a divisional of U.S. patent application Ser. No. 17/055,540, filed on Nov. 13, 2020, with is a U.S. National Phase application and claims priority to and the benefit of International Application Number PCT/CN2018/090345, filed on Jun. 8, 2018, which claims priority to Chinese Patent Application Number 201810468934.6, filed on May 16, 2018, the entire contents of all of which are incorporated herein by reference.

TECHNICAL FIELD

The present invention relates to the field of pharmaceutical preparation, and in particular to an aripiprazole sustained-release microsphere and preparation method therefor.

BACKGROUND OF THE INVENTION

Aripiprazole is a novel atypical anti-schizophrenia drug and a neurotransmitter stabilizer having dual-direction regulation effect on nervous system. The aripiprazole, which has a high affinity for D2, D3, 5-HT1A and 5-HT2A receptors, exerts an anti-schizophrenia effect by exerting partial agonist action at D2 and 5-HT1A receptors and antagonist action at 5-HT2A receptors, thereby treating various types of schizophrenia. According to the foreign clinical trials, aripiprazole has significant effects on the positive and negative symptoms of schizophrenia, and can also improve the concomitant emotional symptoms and reduce the recurrence rate of schizophrenia. However, due to the particularity of patients with schizophrenia, i.e prominent refusal to take drugs and the requirements for long-term medication therapy, there is still a need to develop formulations with improved compliance and long-acting. Long-acting sustained-release microspheres for injection are characterized by reduced frequency of drug administration to patients, convenient administration, better bioavailability, stable blood concentration, no first-pass effect in liver and high compliance, in this regard, long-acting aripiprazole sustained-release microspheres are of great value in clinical.

At present, commercially available long-acting aripiprazol sustained-release formulations are Abilify Maintena and Arista that developed and produced by Otsuka of Japan and ALkermes of the United States respectively. However, those two listed products have the same defect, that is, the effective drug concentration cannot be reached at the early stage of the drug administration due to the low release concentration, and the therapeutic effect should be achieved by taking tablets orally for 14 days after the administration. This administration mode still retains the inconvenience occurring when administrating short-acting drugs in clinical, and an obvious peak-valley phenomenon, which can bring about large side effects and an overdose in the early administration process can be observed.

Patent publication No. CN102133171A filed by ALKERMES discloses an aripiprazole supplied in a micronized and crystallized state, other than aripiprazole microspheres. What's more, the microcrystalline aripiprazole disclosed by the application has a mean diameter between about 30 and 80 microns, which should be injected with 7 or 8 gauge needle (18-21G) according to the syringe needle corresponding to the size of the marketed microsphere products. However, needles with that size have a diameter of 0.5-0.8 mm, and the patients may feel obvious pain when using them for injection. In addition, due to the large particle size of the drug, increased viscosity is needed to keep it in suspension, which in turn leading to difficulty when injecting the suspension. Furthermore, as the suspension formulation is prone to precipitation before injection, operations must be slowly and continuously and the drug must be suspended when sucking the suspension formulation into the syring, otherwise the needle may be clogged. Likewise, complicated operations should also be performed during the injection of the suspension formulation, and improper operations can easily cause the needle to be clogged and thus fail to injection. It can be seen that the entire process of the drug administration must be completed by medical workers who have received special training, resulting in inability to apply the drug widely in general medical institutions, and inconvenience to the promotion of the drug use.

Patent No. CN101742989B filed by Otsuka and Shogo Hiraoka et al. (Preparation and Characterization of High-Content Aripiprazole-Loaded Core-Shell Structure Microsphere for Long-Release Injectable Formulation) relates to microspheres having core/shell structure. However, the disclosed microspheres also have excessively large particle size, and thus, there are still some problems when the microspheres are injected, such as inability to use 5 gauge needle, high requirements for injection operations and high pain sensation of patients. In addition, the microspheres prepared according the method disclosed in the patent may release 10% drug on the first day of administration, which results in a high risk of side effects due to excessive drug concentration; what's more, compared to the microspheres mentioned in the patent, most of which are samples that have been released for more than 2 months, 1 month-released products that being developed due to the serious side effects of prior schizophrenia drugs are more advantageous in terms of safety and timeliness of risk control. While, releasing mode of the developed microspheres having core/shell structure is more dependent on the composition of core. Said releasing mode is relatively simple for controlling drug release, and may lead to concentrated release due to rapid degradation of the shell, or slow drug release due to slow degradation of the shell, or discontinuous release.

Patent No. CN1870980B discloses a preparation method of sterile injectable aripiprazole formulation. However, the preparation process of sterile injectable aripiprazole formulation involved in this patent requires a grinding process and the like, resulting in a long preparation cycle. At the same time, aseptic conditions required in the preparation processes are easy to be destroyed, and thus the preparation method is not suitable for industrial large-scale production.

Microspheres disclosed in patent publication Nos. CN105078898A and CN105310997A have an excessively low drug loading, and long-acting injection formulations of aripiprazole disclosed in patent/patent application Nos. CN102525915B, CN103301461A and CN105012236A contain oil for injection, which will increase the pain of the patient during injection and have less clinical significance.

Particle size of microspheres disclosed in patent publication No. CN106727358A cannot be controlled within 20 μm, resulting in the microspheres cannot be injected with 5 gauge needle. What's more, the release cycle of said microspheres is 2 months.

In "D-Optimal Designing and Optimization of Long Acting Microsphere-Based Injectable Formulation of Aripiprazole" disclosed by Tushar Nahata and Tulsi Ram Saini, an aripiprazole microsphere having a drug loading of within 30% is disclosed, and cannot meet the clinical demand for long-term sustained release.

SUMMARY OF THE INVENTION

The object of the present invention is to provide an aripiprazole sustained-release microsphere, which can rapidly reach an effective drug concentration at the early stage of administration to achieve the therapeutic effect without taking tablets simultaneously. Moreover, the microsphere of the present invention will not show a sudden release. In addition, as the mean particle size of the microsphere of the present invention is less than 20 μm, it can be injected with a 5 gauge needle, thereby the pain of patients can be reduced during injection. Finally, the aripiprazole sustained-release microsphere provided by the present invention are characterized not only by its small particle size, but also by high drug loading, high yield, good spheronization and its ability to adapt to large-scale production.

Therefore, one object of the present invention is to provide an aripiprazole sustained-release microsphere.

Another object of the present invention is to provide a method for preparing the aripiprazole sustained-release microsphere.

Yet another object of the present invention is to provide a suspension formulation comprising the above aripiprazole sustained-release microsphere.

The technical solutions provided by the present invention are as follows.

In one aspect, the present invention provides an aripiprazole sustained-release microsphere, comprising aripiprazole or salts thereof and poly(lactide-co-glycolide)copolymer; wherein, after being dissolved in a solvent B, the microsphere is in a spherical reticulate skeleton structure, small reticular holes are distributed in the sphere; and the aripiprazole or salts thereof are filled in the holes.

The microsphere has a mean particle size of less than 20 μm; the aripiprazole or salts thereof has a content of 65%-80% of the total weight of the microsphere.

Preferably, the solvent B is any solvent capable of dissolving the aripiprazole or its salts; more preferably, the solvent B is 10% acetic acid, 20% acetic acid or 10% ethyl acetate.

Preferably, the microsphere has a mean particle size of 10-13 μm.

Preferably, the aripiprazole or salts thereof has a content of 70%-75% of the total weight of the microsphere; more preferably 71%.

Preferably, the poly(lactide-co-glycolide) copolymer has an intrinsic viscosity of 0.2-0.55 dL/g; more preferably 0.2-0.35 dL/g; and most preferably 0.2 dL/g;

Preferably, the poly(lactide-co-glycolide) copolymer has a polydispersity index of 1.0-3.0; more preferably 1.0-2.0; most preferably 1.5;

Preferably, the poly(lactide-co-glycolide) copolymer has a content of 20%-35%; more preferably 25%-30%; and most preferably 29% of the total weight of the microsphere.

Preferably, the poly(lactide-co-glycolide) copolymer has a weight-average molecular weight of 15000-60000; more preferably 20000-40000; further preferably 20000-30000; and most preferably 25000.

Preferably, the molar ratio of lactide to glycolide in the poly(lactide-co-glycolide) copolymer is 50:50-75:25, more preferably 50:50.

In another aspect, the present invention provides a method for preparing the aripiprazole sustained-release microsphere, the method comprises the following steps:

(1) mixing aripiprazole or salts thereof with poly(lactide-co-glycolide) copolymer, adding with organic solvent A, and then heating to a certain temperature, shaking for dissolving;
(2) mixing the solution obtained from step (1) with a polyvinyl alcohol (PVA) solution under the condition of controlling the evaporation of the organic solvent A, adjusting the pH, and then stirring the mixture under a certain temperature to obtain an emulsion;
(3) solidifying the emulsion obtained from step (2) and evaporating the organic solvent A over a period of time to form microspheres, centrifuging and lyophilizing to obtain the microsphere with a mean particle size of less than 20 μm.

Preferably, in step (1), the ratio of the weight of the aripiprazole or salts thereof and the poly(lactide-co-glycolide) copolymer to the total weight of the aripiprazole or salts thereof, the poly(lactide-co-glycolide) copolymer and the organic solvent A is 9%-25% (w/w).

Preferably, in step (1), the weight ratio of the organic solvent A to the aripiprazole or salts thereof is 4:1-10:1; and more preferably 8:1.

Preferably, in step (1), the weight ratio of the aripiprazole or salts thereof to the poly(lactide-co-glycolide) is 5:2; preferably, in step (1), the organic solvent A is dichloromethane.

Preferably, in step (1), the poly(lactide-co-glycolide) copolymer has an intrinsic viscosity of 0.2-0.55 dL/g; more preferably 0.2-0.35 dL/g; and most preferably 0.2 dL/g.

Preferably, in step (1), the poly(lactide-co-glycolide) copolymer has a polydispersity index of 1.0-3.0; more preferably 1.0-2.0; most preferably 1.5.

Preferably, in step (1), the poly(lactide-co-glycolide) copolymer has a weight-average molecular weight of 15000-60000; more preferably 20000-40000; further preferably 20000-30000; and most preferably 25000.

Preferably, in step (1), the molar ratio of lactide to glycolide in the poly(lactide-co-glycolide) copolymer is 50:50-75:25, more preferably 50:50.

Preferably, in step (1), the certain temperature is 40-65 °C, more preferably 55 °C; in some embodiments, the mixture is difficult to dissolve when the temperature is less than 40 °C; while when the temperature is too high, the control of the experimental process may be affected, and potential safety hazards may be caused easily.

Preferably, in step (1), the shaking is conducted under a condition of heating to 40-65 °C;

Preferably, in step (2), the PVA solution has a concentration of 0.1%-1% (w/v); more preferably 0.5%-1% (w/v); and most preferably 1% (w/v).

Preferably, in step (2), the ratio of the volume (L) of the PVA solution to the weight (g) of the aripiprazole or salts thereof is 0.5-1.5:1; more preferably 1.24:1.

Preferably, in step (2), the volume ratio of the organic solvent A added in step (1) to the PVA solution is 1:40-1:250, more preferably 1:205.

Preferably, in step (2), the pH is 9-14, more preferably, the pH is 10;

Preferably, in step (2), the "under a certain temperature" operation is conducted as: controlling the temperature below 15 °C at the first hour of step (2), and then maintaining the temperature or raising the temperature to 15-30 °C for about 2 hours; more preferably, controlling the temperature to 12 °C at the first hour of step (2).

Preferably, in step (2), the stirring has a stirring rate of 3000 rpm.

Preferably, in step (3), the solidifying operation is conducted for 3 hours.

Preferably, in step (3), the microspheres has a mean particle size of 10-13 μm.

In yet another aspect, the present invention provides a suspension formulation comprising the aripiprazole sustained-release microsphere of the present invention and pharmaceutically acceptable carriers.

Preferably, the pharmaceutically acceptable carriers are selected from the group consisting of suspending agent, pH adjusting agent, isotonic agent, surfactant, water and physiological saline; wherein the suspending agent is selected from the group consisting of sodium carboxymethylcellulose, polyvinyl alcohol, polyvinylpyrrolidone, sodium alginate, and glycerin; the isotonic agent is selected from the group consisting of sodium chloride, glucose, mannitol, and sorbitol; the surfactant is nonionic surfactant, and preferably selected from the group consisting of Polysorbate and Poloxamer.

In some other embodiments, the aripiprazole sustained-release microspheres described in the present invention can be formulated as a/an (injectable) suspension formulation, wherein the suspension formulation comprises the aripiprazole sustained-release microsphere of the present invention and pharmaceutically acceptable carriers, and the pharmaceutically acceptable carriers comprise the following components in percentage by weight: mannitol 0-10%; sodium carboxymethylcellulose 0-5%; and the pH of the suspension formulation is adjusted to 6.5-7.5.

The aripiprazole sustained-release microspheres of the present invention is observed by scanning electron microscope after being dissolved in 20% acetic acid solution, naturally dried, and sprayed with gold. As shown in FIG. 5 and FIG. 6, the microspheres of the present invention are in a spherical reticulate skeleton structure.

The aripiprazole described in the present invention can be crystals, noncrystal of aripiprazole, amorphous aripiprazole, aripiprazole hydrates, or other polymorphs of aripiprazole.

What's more, the present invention also relates to the administration of the aripiprazole sustained-release microspheres of the present invention to a subject in need thereof, the microspheres administrated may release sustainedly aripiprazole in the body of the subject over a period of at least 7 days, 14 days or 1 month.

The present invention has the following advantages:

1. Upon injection, the aripiprazole sustained-release microspheres of the present invention release aripiprazole over a period of at least 1 month, and there is no need to take aripiprazole tablets orally to achieve therapeutic concentration for 14 days after the injection. What's more, the microspheres release aripiprazole steadily in the later stage and the release could be completed within 30 days.
2. Sudden release of a drug in microspheres may lead to a rapid increase in the concentration of the drug in the human body during a short period of time and shorten the period of validity of the drug, which is the key problem limiting the wide application of the microspheres. Generally, the smaller the particle size and the greater the drug loading of a microsphere is, the more serious the sudden release is. However, the above defects are just overcome by the aripiprazole sustained-release microspheres of the present invention through screening the specific raw materials and ratio thereof. Specifically, the active drug in the microspheres of the present invention is well compatible with high-molecular polymer and the porosity of those microspheres is high, thereby solving the defect of sudden release even with a mean particle size of 10 μm and a drug loading of 68%-75%.
3. The prior microspheres, which have a particle size of 20-100 μm can only be administered with a 7 or 8-gauge needle (with an inner diameter of 0.51-0.84 mm), and the patients may feel obvious pain upon injection. In contrary, the microspheres of the present invention have a narrower particle size distribution, good uniformity, and the mean particle size of them is controlled within 20 μm, and thus can be injected with a 5-gauge needle. In view of the consistency of the compliance of the injection solution of the present microspheres with common injection solution, the pain of the patients can be reduced. The needle types are shown in following table 1:

| International standard needle type | Mean particle size/μm | Needle type | Inner diameter/mm |
|---|---|---|---|
| 25 G | 15 | 5 | 0.26 |
| 21 G | 30 | 7 | 0.51 |
| 18 G | 50 | 8 | 0.84 |

4. The suspensions used in the existing microspheres require an increased viscosity to keep the microspheres in suspension state, thereby resulting in difficulty to inject the suspension formulation. Furthermore, as the suspension formulation is prone to precipitation before injection, operations must be slowly and continuously and the drug must be suspended when sucking the suspension formulation into the syring, otherwise the needle may be clogged. Likewise, complicated operations should also be performed during the injection of the suspension formulation, and improper operations can easily cause the needle to be clogged and thus fail to injection. It can be seen that the entire process of the drug administration must be completed by medical workers who have received special training, resulting in inability to apply the drug widely in general medical institutions, and inconvenience to the promotion of the drug use.

The experiments proved that when dissolving microspheres having a mean particle size of less than 20 μm in a suspending agent, the particles of the microspheres can be well dispersed and suspended in the suspending agent for a long time without migration or aggregation. Meanwhile, the well dispersed suspension formulation of the microspheres can be sucked and injected smoothly with a 5-gauge needle. However, in case the mean particle size of the microspheres is greater than 20 μm, precipitation, migration, aggregation and clogging of needle may easily occur.

Specifically, the microspheres of the present invention, which have a mean particle size of less than 20 μm, can suspend easily and well in a suspending agent with low viscosity, thus, this kind of suspension formulation of microspheres is not easy to precipitate, convenient for injection, and convenient for medical personnel to inject, and the pain of the patients can be greatly reduced as it can be injected with a 5-gauge needle.

In addition, the microspheres of the present invention have a particle size span within 1-2 μm, stable quality, and can easily suspend and cannot precipitate or clog a needle upon injection. Therefore, only simple operations are needed and no special training should be received by medical workers, and medical workers in general medical institutions can do those operations.

5. On the premise of ensuring a small particle size, drug loading of the aripiprazole sustained-release microspheres described in the present invention can achieve 65-80%. And during the preparation of the microspheres, less dichloromethane is used, resulting in high solid content and high yield. A yield of 3 g/L can be reached by the preparation method of the present invention, while only 1 g/L of yield can be reached by the preparation methods in prior art.
6. The aripiprazole sustained-release microspheres are in a spherical reticulate skeleton structure, which is beneficial to increase the drug loading of the aripiprazole sustained-release microspheres.
7. The inventors of the present invention screened an optimal ratio of the aripiprazole to the poly(lactide-co-glycolide) through large amount of experiments, and the uniform drug release may be affected no matter the ratio is too high or too low. Moreover, the inventors also found that the control of the time and the temperature of step (2) of the method of the present invention is very important for the experimental results. At the first hour of step (2), API is easy to crystallize and solidify quickly to form into many small crystals if the temperature is too low; while the API is easy to form large crystals which may destroy the microspheres and lead to formation of irregular solid particles under too high temperature.
8. The method for preparing the aripiprazole sustained-release microspheres provided by the present invention is characterized by simple processes, stable and reproducible results, and can be used in industrial large-scale production. Meanwhile, compared to microspheres having a core/shell structure, the sustained-release microspheres which are obtained by the present method and are in a spherical reticulate skeleton structure have obviously smaller particle size and significantly better pharmacodynamics.

BRIEF DESCRIPTION OF THE DRAWINGS

Hereinafter, the embodiments of the present invention will be described with reference to the accompanying drawings in detail, in which.

DETAILED DESCRIPTION OF PREFERRED EMBODIMENTS

The present invention will be further described in detail in combination with the embodiments hereinafter. It will be appreciated by those skilled in the art that the embodiments provided are only used to illustrate the present invention, rather than limiting the scope of the present invention in any way.

Experimental methods in the following embodiments are all conventional methods unless otherwise specified. Raw materials, reagents and other materials used in the following examples can be commercially available unless otherwise specified.

Example 1

50 g of aripiprazole and 20 g of poly(lactide-co-glycolide) copolymer with an intrinsic viscosity of 0.2 dL/g, a polydispersity index of 1.5, a weight-average molecular weight of 25000 and a molar ratio of lactide to glycolide of 50:50 were mixed, and then 400 g (301.9 ml) of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Figure 1:
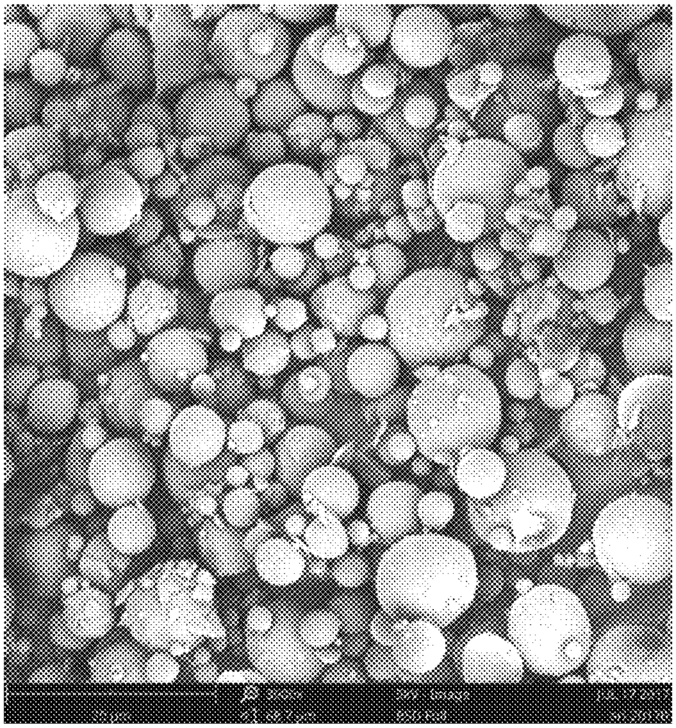
FIG. 1 shows an electron microscope image of the microspheres sample prepared in Example 1.
Figure 5:
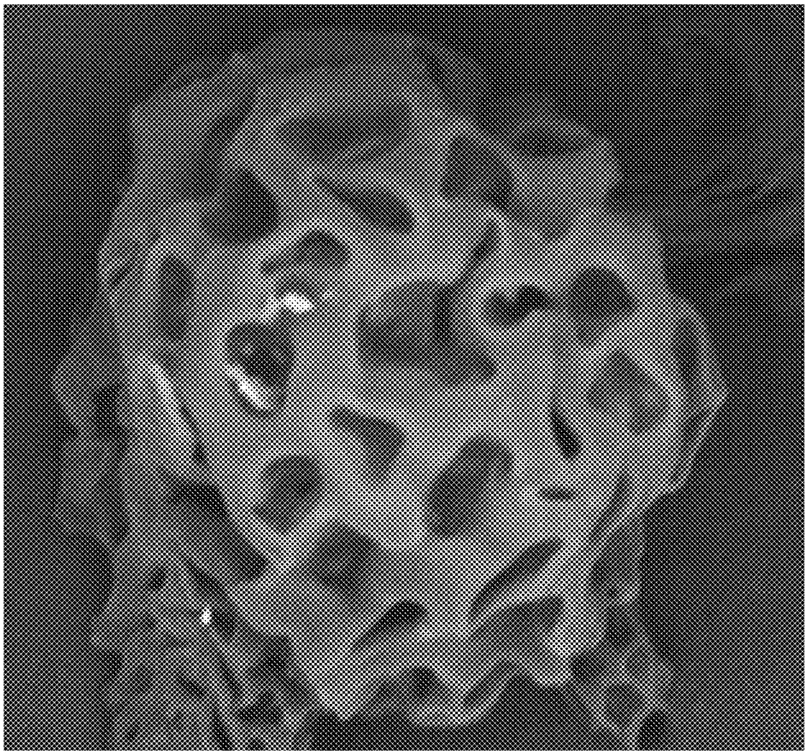
FIG. 5 shows an electron microscope image of the sample obtained by dissolving the microspheres sample prepared in Example 1 with 10% ethyl acetate.

Conclusion: The obtained microspheres had a drug loading of 71% and a yield of 92%. The electron microscope image of the microspheres sample was shown in FIG. 1, from which it could be seen those microspheres had good ballability and smooth and complete surface. What's more, the results shown that the microspheres were in a spherical reticulate skeleton structure (FIG. 5) after being dissolving in 10% ethyl acetate. Aripiprazole in the microspheres released rapidly in the early phase, so as to ensure the effective drug concentration was reached as soon as possible, and in the later phase, it released smoothly and completely within one month.

Example 2

50 g of aripiprazole and 20 g of poly(lactide-co-glycolide) copolymer with an intrinsic viscosity of 0.55 dL/g, a polydispersity index of 3.0, a weight-average molecular weight of 35000, a molar ratio of lactide to glycolide of 50:50 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Figure 2:
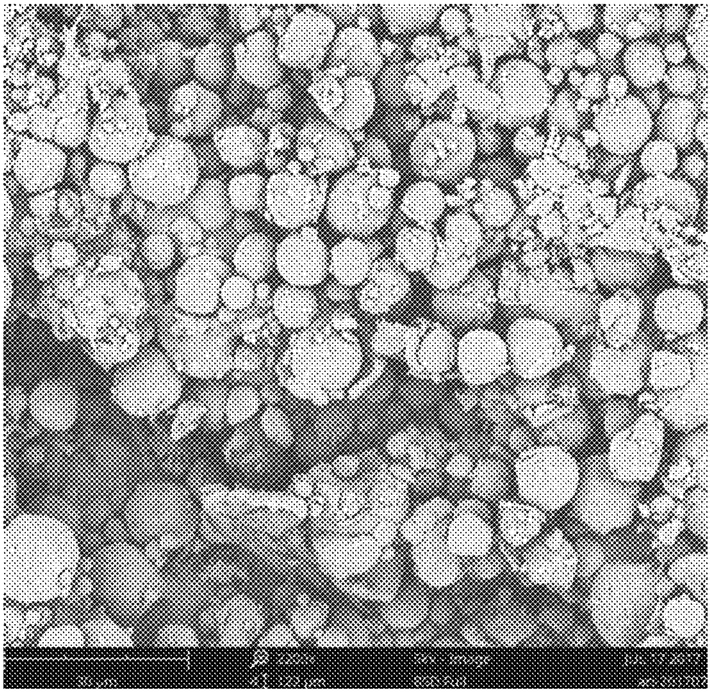
FIG. 2 shows an electron microscope image of the microspheres sample prepared in Example 2.
Figure 6:
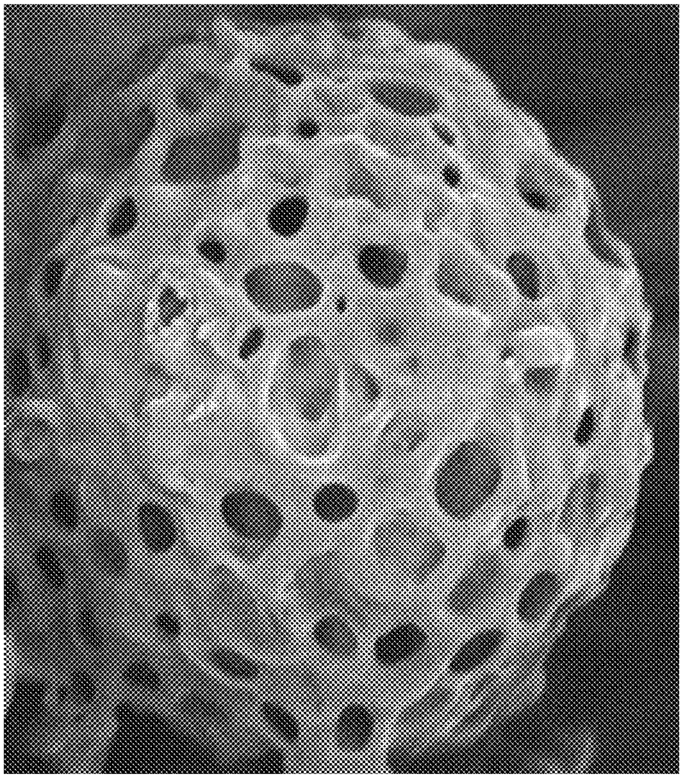
FIG. 6 shows an electron microscope image of the sample obtained by dissolving the microspheres sample prepared in Example 2 with 10% acetic acid.

Conclusion: The obtained microspheres had a drug loading of 70% and a yield of 87%. The electron microscope image of the microspheres sample was shown in FIG. 2, from which it could be seen those microspheres had good ballability and smooth and complete surface. What's more, the results shown that the microspheres were in a spherical reticulate skeleton structure (FIG. 6) after being dissolving in 10% acetic acid. Aripiprazole in the microspheres released rapidly in the early phase, so as to ensure the effective drug concentration was reached as soon as possible, and in the later phase, it released smoothly and completely within one month.

Example 3

50 g of aripiprazole and 20 g of poly(lactide-co-glycolide) copolymer with an intrinsic viscosity of 0.6 dL/g, a polydispersity index of 2.0, a weight-average molecular weight of 75000, a molar ratio of lactide to glycolide of 75:25 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Figure 3:
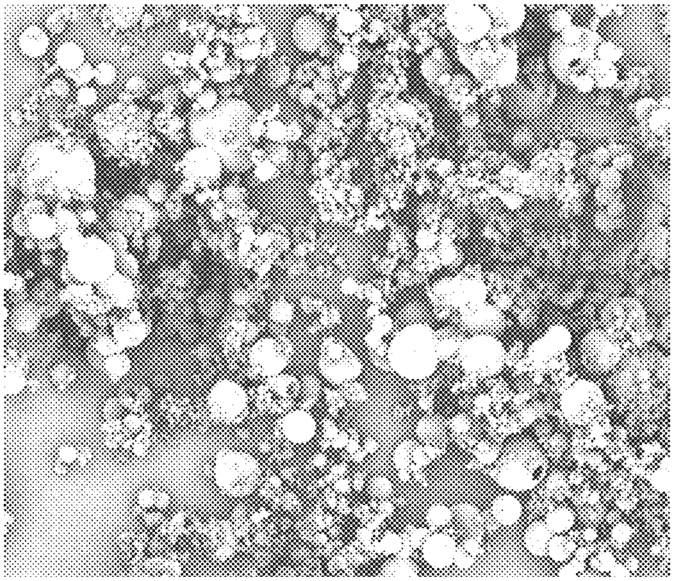
FIG. 3 shows an electron microscope image of the microspheres sample prepared in Example 3.

Conclusion: The obtained microspheres had a drug loading of 68% and a yield of 80%. The electron microscope image of the microspheres sample was shown in FIG. 3, from which it could be seen only a few of the harvested samples form into balls, and most of the samples are irregular particles with poor fluidity.

Example 4

50 g of aripiprazole and 20 g of poly(lactide-co-glycolide) copolymer with an intrinsic viscosity of 0.35 dL/g, a polydispersity index of 1.0, a weight-average molecular weight of 40000, a molar ratio of lactide to glycolide of 65:35 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Figure 4:
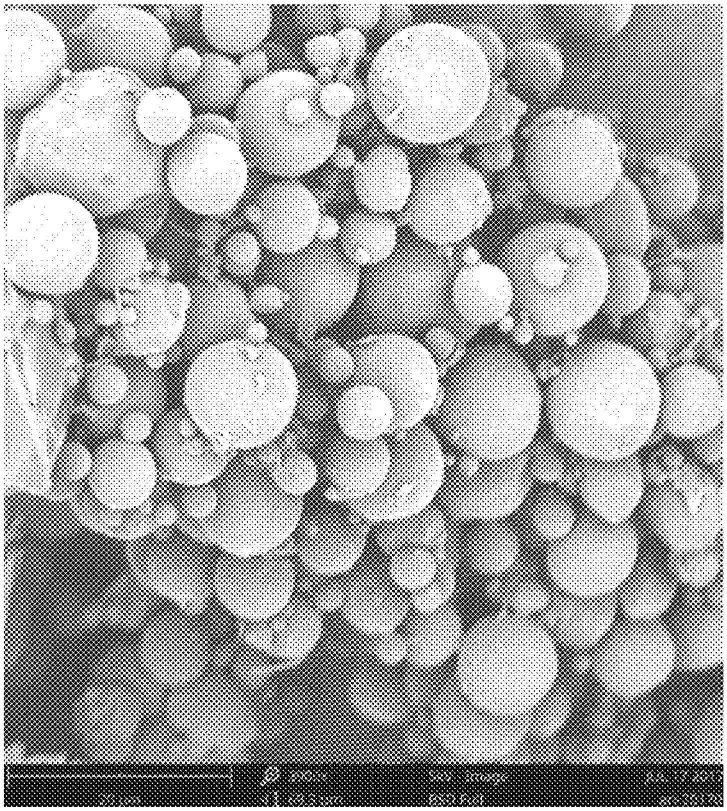
FIG. 4 shows an electron microscope image of the microspheres sample prepared in Example 4.

Conclusion: The obtained microspheres had a drug loading of 72% and a yield of 89.2%. The electron microscope image of the microspheres sample was shown in FIG. 4, from which it could be seen those microspheres had good ballability and smooth and complete surface.

Example 5

50 g of aripiprazole and 20 g of poly(lactide-co-glycolide) copolymer with an intrinsic viscosity of 0.3 dL/g, a polydispersity index of 1.5, a weight-average molecular weight of 20000, a molar ratio of lactide to glycolide of 75:25 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 71.6% and a yield of 93.2%. The results showed that those microspheres had good ballability and smooth and complete surface.

Example 6

50 g of aripiprazole and 20 g of poly(lactide-co-glycolide) copolymer with an intrinsic viscosity of 0.2 dL/g, a polydispersity index of 1.5, a weight-average molecular weight of 40000, a molar ratio of lactide to glycolide of 85:15 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and its temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 65.3% and a yield of 56%. The results showed that those microspheres had bad ballability and a large number of samples adhered to each other with irregular particles and poor fluidity.

Example 7

50 g of aripiprazole and 20 g of poly(lactide-co-glycolide) copolymer with an intrinsic viscosity of 0.6 dL/g, a polydispersity index of 1.5, a weight-average molecular weight of 80000, a molar ratio of lactide to glycolide of 100:0 were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 53% and a yield of 61%. The results showed that no microspheres were formed and there were large amounts of irregular particles and debris with poor fluidity.

Example 8

32 g of aripiprazole (wherein the content of the aripiprazole is 65% of the total weight of the aripiprazole and poly(lactide-co-glycolide) copolymer) and 17 g of poly (lactide-co-glycolide) copolymer (wherein the intrinsic viscosity is 0.35 dL/g, the polydispersity index is 2.0, the weight-average molecular weight is 25000, the molar ratio of lactide to glycolide is 50:50) were mixed, and then 500 g of dichloromethane (9% w/w) was added thereto, the obtained mixture was then heated to 40 °C, shaken to dissolve to obtain a dichloromethane solution. Meanwhile, a 20 L of 0.1% PVA solution was prepared, and the pH of the PVA solution was adjusted to 9 with addition of sodium hydroxide and the temperature was controlled at 15 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 61% and a yield of 86%. The results showed that those microspheres had good ballability, regular, round and smooth surface and good fluidity.

Example 9

50 g of aripiprazole (wherein the content of the aripiprazole is 80% of the total weight of the aripiprazole and poly(lactide-co-glycolide) copolymer) and 12 g of poly (lactide-co-glycolide) copolymer (wherein the intrinsic viscosity is 0.2 dL/g, the polydispersity index is 1.5, the weight-average molecular weight is 30000, the molar ratio of lactide to glycolide is 75:25) were mixed, and then 200 g of dichloromethane (24% w/w) was added thereto, the obtained mixture was then heated to 65 °C, shaken to dissolve to obtain a dichloromethane solution. Meanwhile, a 50 L of 1% PVA solution was prepared, and the pH of the PVA solution was adjusted to 12 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 73% and a yield of 91%. The results showed that those microspheres had good ballability, regular particles, round and smooth surface and good fluidity.

Example 10

50 g of aripiprazole (wherein the content of the aripiprazole is 80%) and 12 g of poly(lactide-co-glycolide) copolymer (wherein the intrinsic viscosity is 0.3 dL/g, the polydispersity index is 2.0, the weight-average molecular weight is 60000, the molar ratio of lactide to glycolide is 75:25) were mixed, and then 250 g of dichloromethane (20% w/w) was added thereto, the obtained mixture was then heated to 65 °C, shaken to dissolve to obtain a dichloromethane solution. Meanwhile, a 62 L of 1% PVA solution was prepared, and the pH of the PVA solution was adjusted to 13 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 76% and a yield of 86%. The results showed that those microspheres had good ballability, regular particles, round and smooth surface and good fluidity.

Example 11

32 g of aripiprazole (wherein the content of the aripiprazole is 65%) and 17 g of poly(lactide-co-glycolide) copolymer (wherein the intrinsic viscosity is 0.2 dL/g, the polydispersity index is 1.0, the weight-average molecular weight is 15000, the molar ratio of lactide to glycolide is 65:35) were mixed, and then 500 g of dichloromethane (9% w/w) was added thereto, the obtained mixture was then heated to 65 °C, shaken to dissolve to obtain a dichloromethane solution. Meanwhile, a 120 L of 1% PVA solution was prepared, and the pH of the PVA solution was adjusted to 14 with addition of sodium hydroxide and its temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

Conclusion: The obtained microspheres had a drug loading of 63% and a yield of 93%. The results showed that those microspheres had good ballability, regular particles, round and smooth surface and good fluidity.

Example 12

Figure 7:
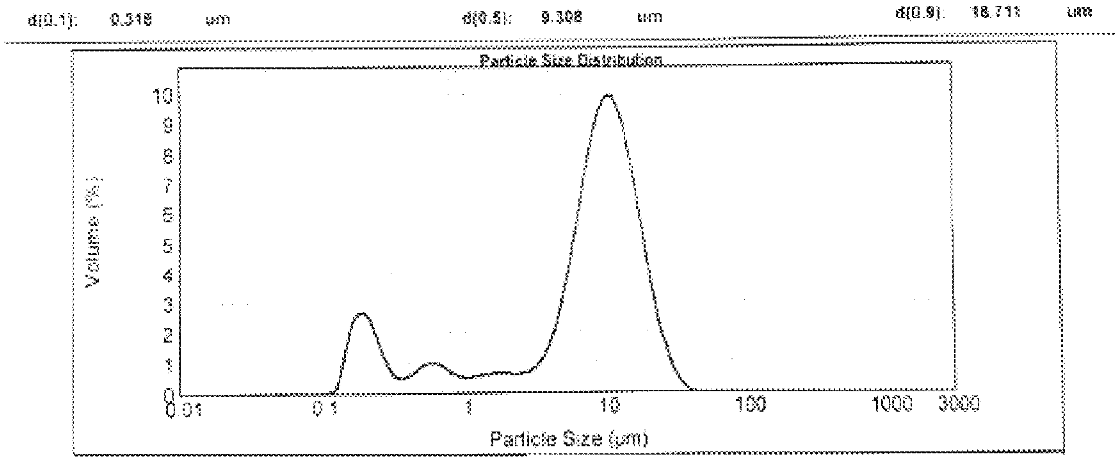
FIG. 7 shows a graph of particle size distribution of the microspheres sample prepared in Example 1.

Aripiprazole sustained-release microspheres were prepared for determining their particle size, and the results were shown in following table 2. In the table, the samples in groups 1-11 were aripiprazole sustained-release microspheres prepared in Examples 1-11 respectively, the samples in group 12 were aripiprazole sustained-release microspheres prepared according to the method disclosed in Example 9 of the patent application No. CN201710052728, and the samples in group 13 were aripiprazole sustained-release microspheres prepared according to the method disclosed in Example 7 of the patent application No. CN200880021585.8. FIG. 7 shows a graph of particle size distribution of the microspheres sample prepared in Example 1 of the present invention.

Determination of the samples: about 25 mg (equivalent to about 20 mg aripiprazole) samples was weighted and placed into a 10 ml penicillin bottle, 5 ml purified water was added with a pipette. The samples were prepared in parallel in duplicate. The optical model was set as Fraunhofer rfd, the purified water was set as the dispersion medium and the rotational speed was set as 2200 rmp. The sample was suspended by ultrasound for 5 min before determination. The sample was removed and shaken up, and then was slowly dropped into the sample cell with a dropper till the shading rate was 5%-10%, the dropping of the sample was stopped, determination was conducted and the results were recoded (each sample was determined for 3 times in parallel and then the results were averaged).

TABLE 2 determination of particle size of aripiprazole sustained-release microspheres

| Group to be tested | Particle size range (D10/D90) | Mean particle size (D50/μm) |
|---|---|---|
| 1 | 0.3/18.7 | 9.3 |
| 2 | 1.5/16.5 | 12.3 |
| 3 | 0.6/86.9 | 35.6 |
| 4 | 3.5/17.2 | 10.6 |
| 5 | 5.9/19.6 | 11.5 |

TABLE 2-continued

| determination of particle size of aripiprazole sustained-release microspheres | | |
|---|---|---|
| Group to be tested | Particle size range (D10/D90) | Mean particle size (D50/μm) |
| 6 | 0.1/125.3 | 48.6 |
| 7 | 0.8/142.6 | 34.2 |
| 8 | 1.2/22.6 | 13.6 |
| 9 | 5.6/21.5 | 16.8 |
| 10 | 1.6/18.9 | 11.6 |
| 11 | 2.8/26.3 | 12.8 |
| 12 | 26.9/87.1 | 48.6 |
| 13 | 32.7/68.1 | 35.9 |

Conclusion: the microspheres in groups 3, 6, 7, 12 and 13 have a mean particle size of greater than 20 μm, and cannot be injected with a 5 gauge needle.

Example 13: Study on the Long-Term Effects in SD Rats after Single-Dose Intramuscular (I.M.) Injection The long-acting aripiprazole microspheres obtained in Example 1 of the present invention were prepared into a formulation according to the following method: some microspheres was weighted and dispersed by a pre-prepared suspension (the suspension comprises 7% mannitol, 5% sodium carboxymethyl cellulose, the pH of the suspension is 6.8), then a pharmaceutical formulation with a solid-to-liquid ratio of 15% (w/v) was prepared. Formulation administered in group A was a formulation of microspheres prepared according to the method of Example 1; Formulation administered in group B was a formulation prepared with the same suspension as above and microspheres prepared according to the method of Example 7 of patent application No. CN200880021585.8; Formulation administered in group C was the formulation administered in group B simultaneously adding with oral aripiprazole tablets (2 mg/kg/day).

The above three groups of formulations were injected into the thigh muscles of the rats at a dose of 25 mg/kg respectively. Meanwhile, the rats in group C were orally administered at a dose of 2 mg/kg/day for the first 14 days after the injection. Blood samples were collected at day 1 (6 hour after the injection), 2, 4, 7, 10, 14, 21, 28, and 35. A drug plasma concentration-time curve of the rats was plotted according to the concentration of the drug in plasma determined by an established LC-MS method to evaluate the relationship between plasma concentration and time.

Figure 8:
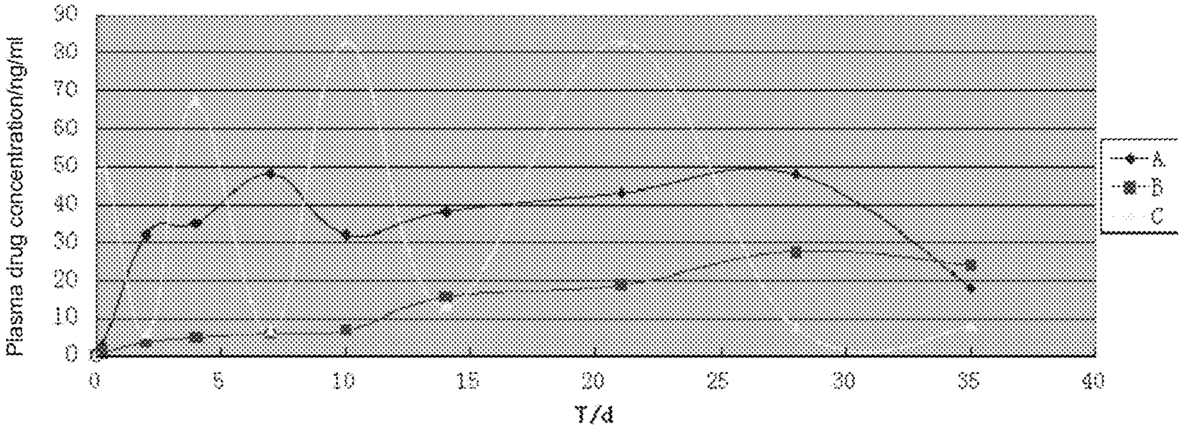
FIG. 8 shows a drug plasma concentration-time curve obtained from rats of Example 13.

Specific results were shown in FIG. 8.

The results showed that the curve for group A was relatively flat, the plasma drug concentration was kept in an effective range during the administration and then decreased after 30 days, indicating that the drug was released completely. The curve for group B showed that the drug sustained release time was longer, which is more than one month, and the drug concentration increased slowly in the early stage and a delayed release phenomenon was observed. In Group C, the drug is administered orally, there is a significant fluctuations in drug plasma concentration with the occurrence of an obvious "peak-valley" phenomenon.

Example 14

The aripiprazole sustained-release microspheres obtained in Examples 1, 2, 4, 5, 8 and 9 of the present invention were prepared into formulations according to the following method: some microspheres was weighted and dispersed by a pre-prepared suspension (the suspension comprises 7% mannitol, 5% sodium carboxymethyl cellulose, the pH of the suspension is 6.8), then a pharmaceutical formulation with a solid-to-liquid ratio of 15% (w/v) was prepared. Microspheres used in each group were prepared according to the corresponding examples.

TABLE 3

| Corresponding relationship between the group and the example | |
|---|---|
| Group | Corresponding example |
| A | Example 1 |
| B | Example 2 |
| C | Example 4 |
| D | Example 5 |
| E | Example 8 |
| F | Example 9 |

Formulations of the above groups were injected into the thigh muscles of the rats at a dose of 25 mg/kg respectively. Blood samples were collected at day 1 (6 hour after the injection), 2, 4, 7, 10, 14, 21, 28, and 35. A drug plasma concentration-time curve of the rats was plotted according to the concentration of the drug in plasma determined by an established LC-MS method to evaluate the relationship between plasma concentration and time.

Figure 9:
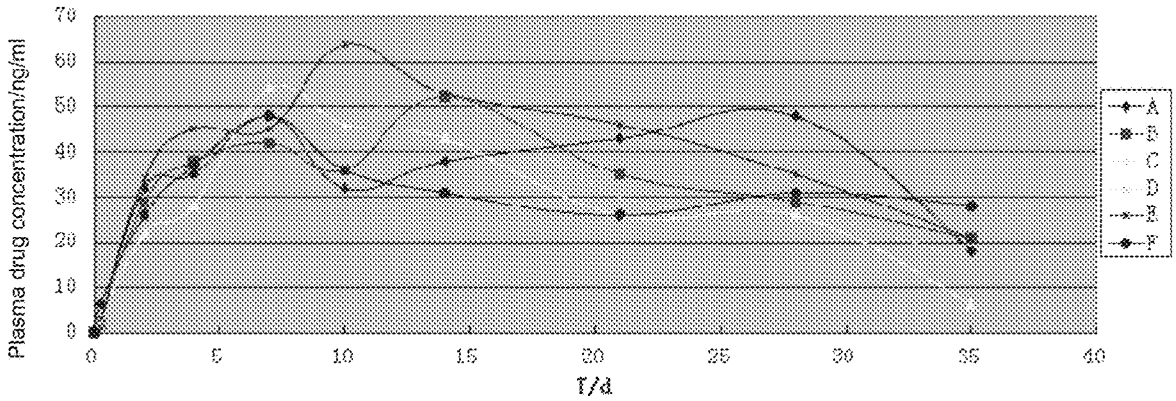
FIG. 9 shows a drug plasma concentration-time curve obtained from rats of Example 14.

Specific results were shown in FIG. 9.

The results showed that the curve for group A was flat, the plasma drug concentration was kept in an effective range during the administration and then decreased after 28 days, indicating that the drug was released completely. The curve for group B was similar to that for group A, in which the plasma drug concentration was also kept in an effective range even though decreased rapidly after 20 days; The curve for group C was similar to that for group B, in which the plasma drug concentration was also kept in an effective range even though decreased rapidly after 20 days; the curves for groups D, E and F were flat during the administration, in which the plasma drug concentration was also kept in an effective range even though decreased rapidly at the later stage.

Example 15

The long-acting aripiprazole microspheres obtained in Example 1 of the present invention were prepared into a formulation according to the following method: some microspheres was weighted and dispersed by a pre-prepared suspension (the suspension comprises 7% mannitol, 5% sodium carboxymethyl cellulose, the pH of the suspension is 6.8), then a pharmaceutical formulation with a solid-to-liquid ratio of 15% (w/v) was prepared. Formulation administered in group A was a formulation of microspheres prepared according to the method of Example 1; Formulation administered in group B was a formulation prepared with the same suspension as above and microspheres prepared according to the method of Example 9 of patent application No. CN201710052728; Formulation administered in group C was a formulation prepared with the same suspension as above and microspheres prepared according to the method of Example 1 of patent application No. CN201410219991.

The above three groups of formulations were injected into the thigh muscles of the rats at a dose of 25 mg/kg respectively. Blood samples were collected at day 1 (6 hour after the injection), 2, 4, 7, 10, 14, 21, 28, and 35. A drug plasma concentration-time curve of the rats was plotted according to the concentration of the drug in plasma determined by an established LC-MS method to evaluate the relationship between plasma concentration and time.

Figure 10:
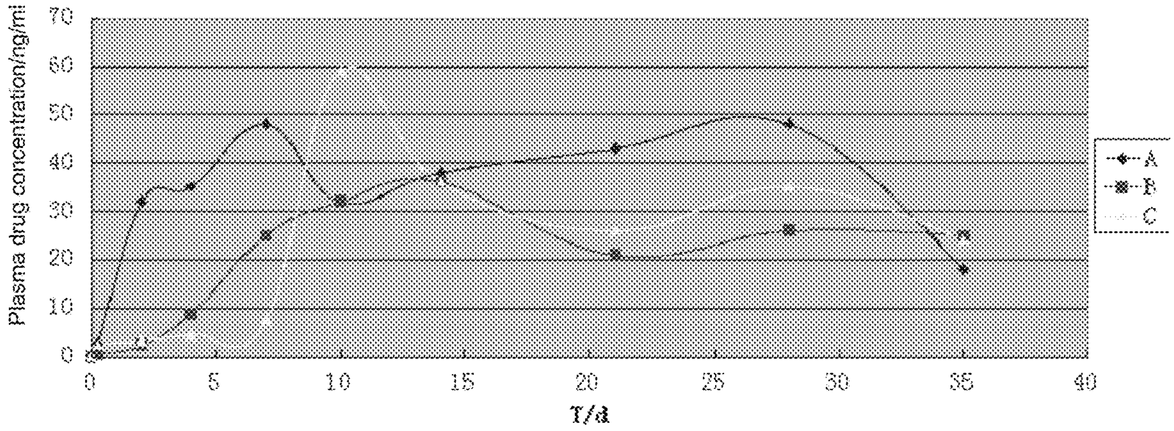
FIG. 10 shows a drug plasma concentration-time curve obtained from rats of Example 15.

Specific results were shown in FIG. 10.

The results showed that the curve for group A was flat, the plasma drug concentration was kept in an effective range during the administration and then decreased after 28 days, indicating that the drug was released completely. Plasma drug concentration for group B showed a delayed release phenomenon at the first 5 days, which was increased slowly and reached the effective concentration at the later stage. Plasma drug concentration in group C showed a delayed release phenomenon at the first 7 days, which was increased rapidly and reached the effective concentration at the later stage.

Example 16: Screening of PVA Concentration 50 g of aripiprazole and 20 g of poly(lactide-co-glycolide) copolymer (wherein the intrinsic viscosity is 0.3 dL/g, the polydispersity index is 1.5, the weight-average molecular weight is 25000, the molar ratio of lactide to glycolide is 50:50) were mixed, and then 400 g of dichloromethane was added thereto, the obtained mixture was then heated to 55 °C, shaken to dissolve to obtain a dichloromethane solution.

Meanwhile, a 62 L of PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

TABLE 4

Effect of different concentration of the PVA solution on the experimental results

| Concentration of the PVA solution | Description of the experimental results |
|---|---|
| 0.05% | The microspheres aggregated and adhered to each other with low ballability |
| 0.1% | General ballability |
| 0.5% | Better ballability |
| 1.0% | The microspheres had good ballability and smooth and complete surface |
| 1.5% | General ballability |

Conclusion: optimal experimental results could be obtained when the PVA concentration was between 0.1% and 1.0%, and the obtained microspheres had good ballability and smooth and complete surface.

Example 17: Effect of Temperature on the Experimental Results 50 g of aripiprazole and 20 g of poly(lactide-co-glycolide) polymer (the intrinsic viscosity is 0.3 dL/g, the polydispersity index is 1.5, the weight-average molecular weight is 25000, the molar ratio of lactide to glycolide is 50:50) were mixed, and then 400 g of dichloromethane was added thereto, the obtained mixture was then heated to 55 °C, shaken to dissolve to obtain a dichloromethane solution. Meanwhile, a 62 L of 1% PVA solution was prepared, and the pH of the PVA solution was adjusted to 10 with addition of sodium hydroxide and the temperature was controlled at a certain temperature. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

TABLE 5

Effect of different temperatures on the experimental results

| Temperature/°C | Description of the experimental results |
|---|---|
| 5 °C | Crystallization and solidification were rapid, micro-crystals were formed |
| 10 °C | Crystallization and solidification were rapid, micro-crystals were formed |
| 12 °C | Crystallization and solidification were rapid, micro-crystals were formed |
| 15 °C | Crystallization and solidification were rapid, micro-crystals were formed |
| 20 °C | Crystallization and solidification were slow, irregular solid particles were formed |

Conclusion: The aripiprazole crystallized quickly and formed into small crystals when the temperature was lower than 15 °C, and thus microspheres with good appearance and optimal experimental results were obtained.

Example 18: Effect of the Amount of Dichloromethane on the Experimental Results 50 g of aripiprazole and 20 g of poly(lactide-co-glycolide) copolymer (wherein the intrinsic viscosity is 0.3 dL/g, the polydispersity index is 1.5, the weight-average molecular weight is 25000, the molar ratio of lactide to glycolide is 50:50) were mixed, and then certain amount of dichloromethane was added thereto, the obtained mixture was then heated to 55 °C, shaken to dissolve to obtain a dichloromethane solution.

Meanwhile, a 62 L of 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

TABLE 6

Effect of different amount of dichloromethane on the experimental results

| Amount of dichloromethane | Ratio of dichloromethane to aripiprazole (by weight) | Description of the experimental results |
|---|---|---|
| 150 g | 3:1 | Bad ballability |
| 200 g | 4:1 | drug loading: 72.8%, yield: 85%, mean particle size: 15.9 μm |
| 400 g | 8:1 | drug loading: 71%, yield: 92%, mean particle size: 9.3 μm |
| 500 g | 10:1 | drug loading: 73.2%, yield: 89%, mean particle size: 7.5 μm |

TABLE 6-continued

| Effect of different amount of dichloromethane on the experimental results | | |
|---|---|---|
| Amount of dichloromethane | Ratio of dichloromethane to aripiprazole (by weight) | Description of the experimental results |
| 600 g | 12:1 | drug loading: 67.3%, yield: 75%, bad ballability |
| 800 g | 14:1 | drug loading: 42.0%, yield: 60%, bad ballability |

Figure 11:
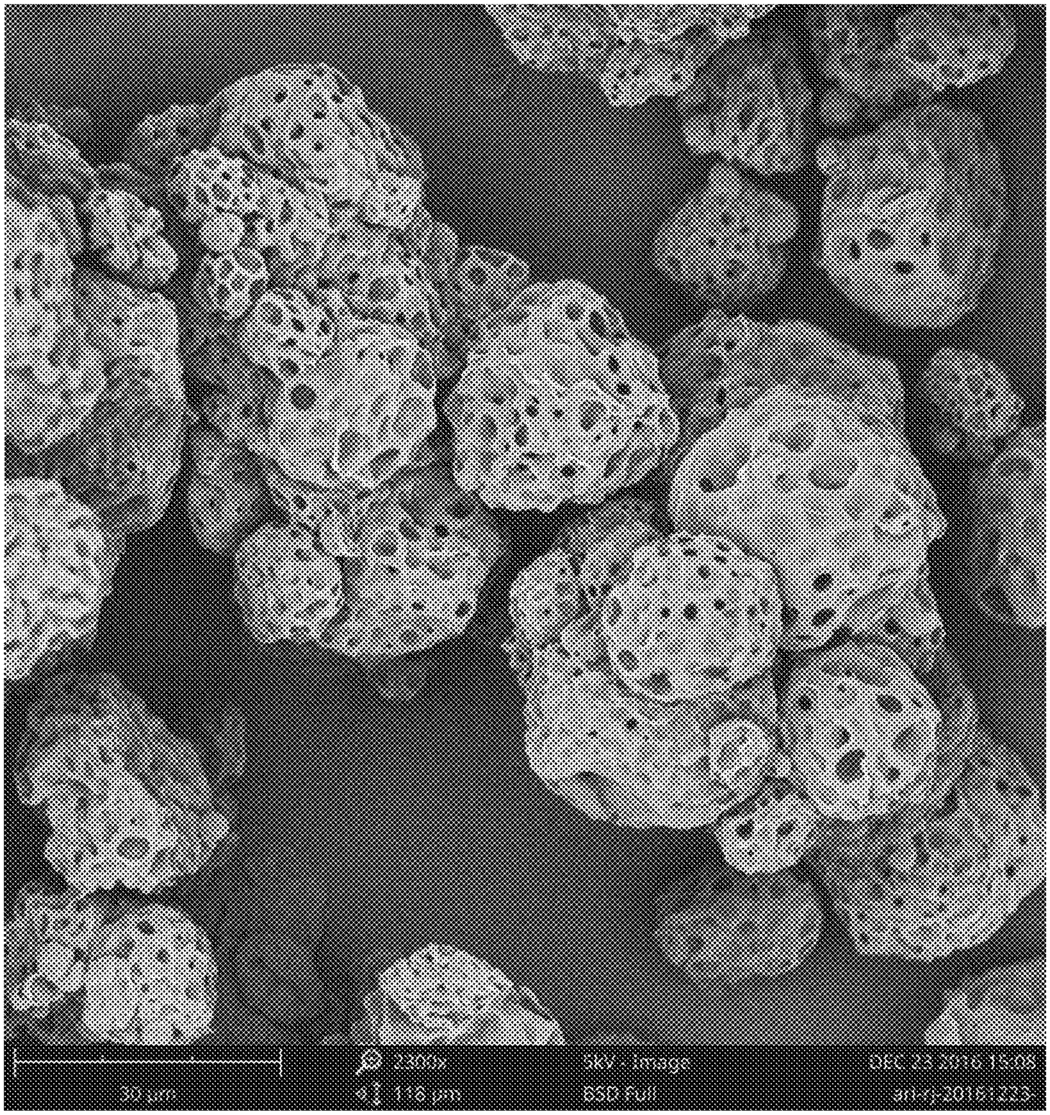
FIG. 11 shows an electron microscope image of the microspheres sample.

Conclusion: It could be seen from the experimental data in table 6 that the experiment proceeded smoothly and the resulting microspheres were qualified when the ratio of dichloromethane to aripiprazole was 4:1-10:1; and optimal experimental result was obtained when said ratio was 8:1. FIG. 11 showed an electron microscope image of the microspheres prepared with 800 g of dichloromethane.

Example 19: Effect of the Amount of PVC Solution on the Experimental Results 50 g of aripiprazole and 20 g of poly(lactide-co-glycolide) polymer (the intrinsic viscosity is 0.3 dL/g, the polydispersity index is 1.5, the weight-average molecular weight is 25000, the molar ratio of lactide to glycolide is 50:50) were mixed, and then 400 g of dichloromethane was added thereto, the obtained mixture was then heated to 55 °C, shaken to dissolve to obtain a dichloromethane solution.

Meanwhile, a certain amount of a 1% PVA solution was prepared, and the pH of the PVA solution was adjusted to 10 with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

TABLE 7

| Effect of different amount of PVC solution on the experimental results | | |
|---|---|---|
| Amount of PVA solution (L) | Ratio of PVA to aripiprazole (L:g) | Description of the experimental results |
| 15 | 0.3:1 | Broken occurred and almost no microspheres were formed |
| 25 | 0.5:1 | good ballability and smooth surface |
| 50 | 1:1 | good ballability and smooth surface |
| 60 | 1.2:1 | good ballability and smooth surface |
| 75 | 1.5:1 | good ballability and smooth surface |

Conclusion: It could be seen from the experimental results of table 7 that very poor experimental results were obtained when the ratio of PVA to aripiprazole was less than 0.5:1.

Example 20: Effect of the pH on the Experimental Results 50 g of aripiprazole and 20 g of poly(lactide-co-glycolide) polymer (the intrinsic viscosity is 0.3 dL/g, the polydispersity index is 1.5, the weight-average molecular weight is 25000, the molar ratio of lactide to glycolide is 50:50) were mixed, and then 400 g of dichloromethane was added thereto, the obtained mixture was then heated to 55 °C, shaken to dissolve to obtain a dichloromethane solution.

Meanwhile, a 62 L of 1% PVA solution was prepared, and the pH of the PVA solution was adjusted with addition of sodium hydroxide and the temperature was controlled at 12 °C. Subsequently, the dichloromethane solution was dispersed in the PVA solution by using a high-speed emulsification equipment or a static mixer with a stirring rate of 3000 rpm. The resulting emulsion was solidified for 3 hours, centrifuged and lyophilized to harvest the microspheres.

TABLE 8

| Effect of different pH on the experimental results | |
|---|---|
| PH | Description of the experimental results |
| 7 | Low ballability |
| 8 | Low ballability |
| 9 | good ballability and smooth surface |
| 10 | good ballability and smooth surface |
| 12 | good ballability and smooth surface |

Conclusion: Poor experimental results might be obtained when the pH was lower than 9.

What is claimed is:

1. A method for preparing an aripiprazole sustained-release microsphere, the method comprising the following steps:

(1) mixing aripiprazole or salts thereof with poly(lactide-co-glycolide) copolymer, adding with an organic solvent A, then heating to a certain temperature, and shaking for dissolving to provide a solution;

(2) mixing the solution obtained from step (1) with a polyvinyl alcohol (PVA) solution to provide a mixture under a condition of controlling evaporation of the organic solvent A, adjusting the pH, and then stirring the mixture under a certain temperature to obtain an emulsion; and (3) solidifying the emulsion obtained from step (2) to microspheres and evaporating the organic solvent A over a period of time to form microspheres, centrifuging and lyophilizing to obtain the microspheres with a mean particle size of less than 20 μm, wherein, in steps (1), (2) and (3), the organic solvent A is dichloromethane;

in step (1), the certain temperature is 40-65 °C;

in step (2), the pH is 9-13; and in step (2), the "under a certain temperature" operation is conducted as:

controlling the temperature below 15 °C.

2. The method according to claim 1, wherein, in step (1), a ratio of a weight of the aripiprazole or salts thereof and the poly(lactide-co-glycolide) copolymer to a total weight of the aripiprazole or salts thereof, the poly(lactide-co-glycolide) copolymer and the organic solvent A is 9%-25% (w/w).

3. The method according to claim 1, wherein, in step (1), a weight ratio of the organic solvent A to the aripiprazole or salts thereof is 4:1-10:1.

4. The method according to claim 1, wherein, in step (1), a weight ratio of the aripiprazole or salts thereof to the poly(lactide-co-glycolide) copolymer is 5:1.2-2.

5. The method according to claim 1, wherein, in step (1), the poly(lactide-co-glycolide) copolymer has an intrinsic viscosity of 0.2-0.55 dL/g;

or, in step (1), the poly(lactide-co-glycolide) copolymer has a polydispersity index of 1.0-3.0;

or, in step (1), the poly(lactide-co-glycolide) copolymer has a weight-average molecular weight of 15000-60000;

or, in step (1), a molar ratio of lactide to glycolide in the poly(lactide-co-glycolide) copolymer is 50:50-65:35.

6. The method according to claim 1, wherein, in step (1), the certain temperature is 55 °C.

7. The method according to claim 1, wherein, in step (2), the PVA solution has a concentration of 0.1%-1% (w/v).

8. The method according to claim 1, wherein, in step (2), the pH is 10.

9. The method according to claim 1, wherein, in step (2), "a certain temperature" operation is conducted as: controlling the temperature to 12 °C.

10. The method according to claim 1, wherein in step (3), the microspheres have a mean particle size of 9-13 μm.

11. The method according to claim 3, wherein, in step (1), the weight ratio of the organic solvent A to the aripiprazole or salts thereof is 8:1.

12. The method according to claim 4, wherein, in step (1), the weight ratio of the aripiprazole or salts thereof to the poly(lactide-co-glycolide) copolymer is 5:2.

13. The method according to claim 5, wherein, in step (1), the poly(lactide-co-glycolide) copolymer has an intrinsic viscosity of 0.2-0.35 dL/g.

14. The method according to claim 5, wherein, in step (1), the poly(lactide-co-glycolide) copolymer has a polydispersity index of 1.5-2.0.

15. The method according to claim 5, wherein, in step (1), the poly(lactide-co-glycolide) copolymer has a weight-average molecular weight of 20000-40000.

16. The method according to claim 15, wherein, in step (1), the poly(lactide-co-glycolide) copolymer has a weight-average molecular weight of 25000.

17. The method according to claim 5, wherein, in step (1), the molar ratio of lactide to glycolide in the poly(lactide-co-glycolide) copolymer is 50:50.

18. The method according to claim 7, wherein, in step (2), the PVA solution has a concentration of 0.5%-1% (w/v).

19. The method according to claim 18, wherein, in step (2), the PVA solution has a concentration of 1% (w/v).

20. The method according to claim 9, wherein, in step (2), the "under a certain temperature" operation is conducted as: controlling the temperature to 12 °C at the first hour of step (2).

* * * * *